United States Patent [19]

Blair et al.

[11] Patent Number: 4,869,589

[45] Date of Patent: Sep. 26, 1989

[54] AUTOMATED VISUAL SCREENING SYSTEM

[75] Inventors: David J. Blair, Springfield, Mass.; Kathy L. Izzarelli, Canterbury, Conn.; Eric J. Albetski, Vernon, Conn.; Cyr J. Parent, Unionville, Conn.

[73] Assignee: United Technologies Corporation, Hartford, Conn.

[21] Appl. No.: 126,807

[22] Filed: Nov. 30, 1987

[51] Int. Cl.⁴ ............................................. A61B 3/02
[52] U.S. Cl. .................................. 351/243; 351/244
[58] Field of Search ............... 351/200, 201, 202, 243, 351/242, 244

[56] References Cited

U.S. PATENT DOCUMENTS

| | | | |
|---|---|---|---|
| 3,905,688 | 9/1975 | Decker et al. | 351/30 |
| 3,969,020 | 7/1976 | Lynn et al. | 351/17 |
| 4,239,351 | 12/1980 | Williams et al. | 351/243 |
| 4,285,580 | 8/1981 | Murr | 351/243 |
| 4,634,243 | 1/1987 | Massof et al. | 351/243 |

FOREIGN PATENT DOCUMENTS

3444580  6/1986  Fed. Rep. of Germany.

Primary Examiner—Rodney B. Bovernick
Assistant Examiner—P. M. Dzierzynski
Attorney, Agent, or Firm—Troxell K. Snyder

[57] ABSTRACT

A visual deficiency screening system (8) includes a display (14) and a means (10, 18) for generating a series of randomly differing images (12). A hood (24) and eyepiece (26) are provided for properly positioning a test subject relative to the display (14).

9 Claims, 5 Drawing Sheets

AUTOMATED VISUAL SCREENING SYSTEM

FIELD OF THE INVENTION

The present invention relates to visual testing.

BACKGROUND

The need for screening of individuals to establish certain minimum visual skills is well established in industry. This need is especially acute for persons serving as visual inspectors wherein an article of manufacture or the like is approved or disapproved based upon a visual inspection conducted by such person. Other individuals whose performance relies on various visual skills include pilots, welders, machinists, etc.

Recent trends in industry have given rise to "self inspection" of finished articles wherein the worker producing the article also is responsible for the inspection thereof. In order to qualify as a visual inspector, it is frequently required that the worker undergo some form of visual skills testing to establish at least a minimum level of proficiency required for the particular inspection to be performed. The administration of such visual skills testing to a significant portion of the workforce at a large industrial location will be appreciated by those skilled in the art as being a significant burden on the local health care facility usually charged with such testing.

Traditional methods of testing, for example, visual acuity, rely on the standard eye chart held a fixed distance from the test subject's eyes. The chart is inscribed with rows or columns of letters or E-shaped figures oriented variously and which the subject must either read or indicate the orientation of each shape. Levels of visual acuity skills are demonstrated by properly describing characters of a certain size on the chart.

Even this simple test has several drawbacks when applied to a large number of test subjects. First, administration of the test requires not only the presence of the test subject, but also a trained test administrator who typically directs the test subject, records the subject's responses, and may even analyze those responses for determining whether or not the subject has demonstrated the required visual acuity skills. Another drawback to the traditional eye chart and derivatives thereof is that the test is essentially the same for all subjects, leading to the possibility that an individual may obtain advanced knowledge of the arrangement of characters and merely recite the characteristics from memory rather than by observation during the test.

Other visual skills which may be tested, for example color recognition and depth perception, require an equal or greater time commitment by both the test subject and the test administrator. For an industrial site having several thousands of individuals who must be periodically screened for minimum visual requirements, the cost in terms of lost production and additional medical personnel required can be prohibitive.

Another level of complexity occurs when the required level of visual skills varies from worker to worker, thus requiring modification of the visual skills screening testing depending upon the individual requirements. A further perspective on the overall testing requirement is gained by noting that despite all the complexity of the various screening tests, changing requirements, interpretation of results, there will typically be only a very small percentage of test subjects whose vision has deteriorated such since the last screening test as to require corrective equipment or decertification.

What is needed is a system and means for conducting visual skills screening of a large number of individuals for identifying those individuals who require further testing by a skilled vision professional.

SUMMARY OF THE INVENTION

It is therefore an object of the present invention to provide a test means and method for automatically screening individuals for visual deficiencies.

It is further an object of the present invention to provide a visual deficiency screening means able to selectively test for a plurality of deficiencies.

It is still further an object of the present invention to provide a screening means adaptable to select, based upon individual requirements, among the plurality of testable deficiencies for administering a specific test program for the tested individual.

According to the present invention, a visual testing system able to automatically screen individual persons for visual defects is provided. The system generates a plurality of visual images on a video display, and records the responses of the test subject for evaluation against a corresponding preselected standard for determining adequacy of visual performance.

More particularly, the present invention provides a software driven system having a color video display linked to a visual image generator such as a laser disk reader or the like, the visual image being selected, or alternatively modified or generated, by a mini computer having a human interface in the form of a keyboard, mouse, touch sensitive panel, etc. The system evaluates one or more visual skills of a test subject by displaying corresponding images on the video monitor and querying the test subject with regard thereto. Each test may be specifically designed to measure the appropriate visual skill, with the subject's responses being evaluated against a preselected test standard for determining if further testing is required. For example, visual acuity at close distances is tested, according to the preferred embodiment of the present invention, by generating a series of individual images having a randomly differing visual characteristic. The system according to the present invention queries the test subject who observes the series of images and responds, via the human interface, based on the observed characteristic for each image.

Depending upon the visual skills of the subject, the size of the images, optical characteristics of the video display, etc., the subject may not be able to accurately indicate the visual characteristic for each image. The system according to the present invention scores the test subject responses against the actual characteristic of the images, and compares the accuracy of such responses to a preselected level of accuracy for determining if the subject has demonstrated adequate visual acuity skills.

It is a feature of the screening system according to the present invention that the plurality of visual skills tested thereby may be selectively employed by the system in response to the requirements of the test subject. For example, a first subject may require testing for only close range visual acuity, while a second test subject would require a full range of visual testing, possibly comprising close range visual acuity, color recognition, and depth perception. The system, responsive to identification information supplied by the test subject, chooses among the plurality of available test sequences, selecting the proper test package for each individual.

One advantage of the screening system according to the present invention is the reduction of labor, at least for the screening testing. The system may be located adjacent a work area where individual test subjects may quickly reach the system and undergo testing when convenient. Only if a test subject is identified by the system as being potentially visually deficient is it necessary to schedule an appointment with an eye care professional for a complete diagnostic test.

Another advantage of the system according to the present invention is the random generation of individual images during certain types of testing which reduces the likelihood that a test subject may memorize the test sequence in advance and simply respond by wrote rather than visual skills. For those tests which produce randomly generated characteristics, each test is, in effect, different from each prior and succeeding test and thus cannot be predicted or memorized in advance.

Both these and other objects and advantages of the testing system according to the present invention will be apparent to those skilled in the art upon review of the following specification and the appended claims and drawing figures.

DETAILED DESCRIPTION OF THE INVENTION

Figure 1:
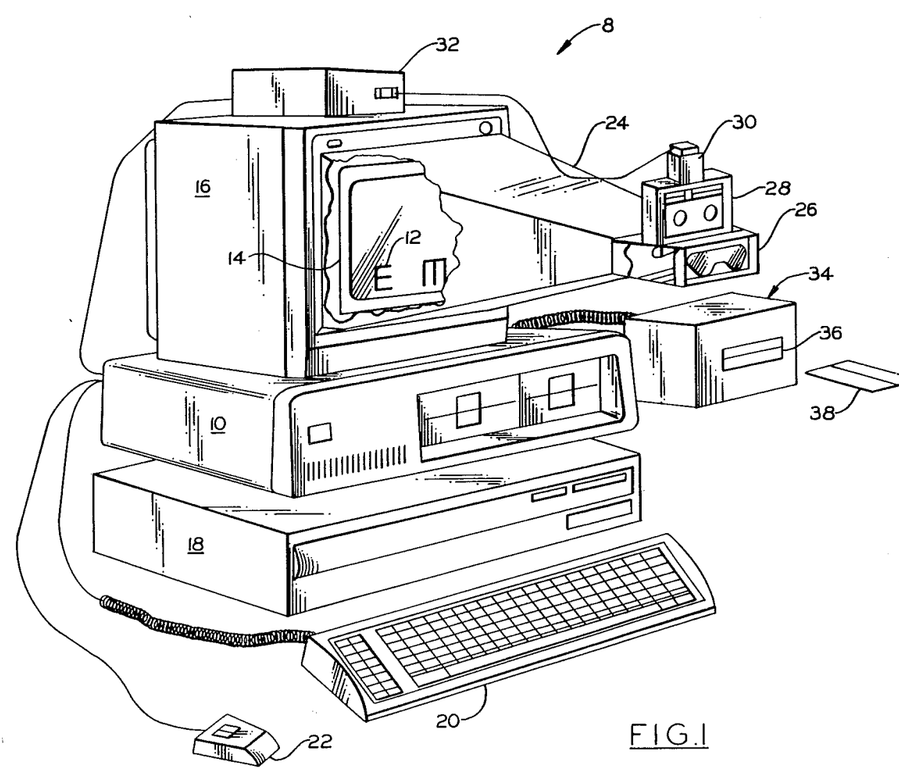
FIG. 1 shows a visual deficiency screening system according to the present invention.

Referring to the drawing figures, and in particular to FIG. 1 thereof, the system according to the present invention is seen to include a number of electronic and electromechanical components linked to cooperatively define the screening system according to the present invention. In the preferred embodiment 8, the system comprises a color video monitor 16, a mini computer 10, a laser disk player 18, and one or more user or subject interfaces 20, 22.

The mini computer 10 is provided with a collection of software files for directing the operation of the system 8, conducting the test and evaluating the responses of the test subject as discussed hereinbelow. The components 10, 16, 18, 20, 22 are illustrated as individual components connected by multiple wire cables or the like as is typical for mini computers and their associated peripherals.

The color monitor 16 includes a fixed hood 24 covering the display 14 of the monitor 16 thus requiring the test subject to view the display 14 only through the eye piece 26 provided in the hood 24. The eye piece 26 and hood 24 may also include one or more visual filters 28 which may be positioned by an actuator 30 and actuator controller 32 in response to command signals initiated by the mini computer 10. Such filters 28 may include optical lenses for changing the optical characteristics of the eye piece-hood-display configuration, color tint filters, shading filters, and other modifiers for altering the images 12 appearing on the display 14. The filters 28 and actuator 30 may be adapted to operate independently with regard to the left and right eyes of the test subject, thus allowing screening of each eye independently.

During a screening test of an individual test subject, the mini computer 10 displays a collection of images 12 on the display 14 and queries the test subject, either verbally via a speaker system (not shown) or visually by displaying a written query on the display 14 which is read by the subject viewing the display 14 through the eye piece 26. Visual images 12 on the display 14 are produced responsive to a video input delivered from the laser disk player 18 as controlled and/or modified by the mini computer 10, or alternatively, generated wholly by the mini computer 10 based upon the software construction set for the particular visual defect screening test being applied.

It should be noted that the laser disk player 18 utilizes a visual storage medium having a series of individual frames which are "played" on the video monitor 16 in response to instructions from the mini computer 10. It is possible to generate the necessary video signal wholly within the mini computer 10, eliminating the laser disk player 18. Such mini computer systems are typically more complex and hence expensive, thus the combination laser disk player 18 and mini computer 10 are intended to jointly illustrate a means for selectively generating the desired series of visual images in the system according to the present invention in partial fulfillment of applicants' duty of full disclosure and of disclosure of the preferred embodiment of the present invention, and thus should not be interpreted as restricting such video image generating means to a multiple component system as disclosed herein.

In response to the query of the system 8, the test subject responds via the human interfaces such as the keyboard 20 or mouse 22 illustrated in FIG. 1. As above, the interfaces 20, 22 are merely intended to be illustrative as interface means, and would additionally include such practical interfaces as touch sensitive pads, light pens, or perhaps even voice recognition systems wherein verbal commands of the test subject are converted to information signals which may be meaningfully interpreted by the mini computer 10.

An additional feature and component of the system 8 according to the present invention is a means for recognizing each individual test subject and tailoring the visual screening testing thereof in response to the job and/or other requirements specific to that individual test subject. One such means is illustrated in FIG. 1 by the identity card reader 34 linked to the mini computer 10 and having a slot 36 for accepting a coded card 38. For a system 8 adapted to screen a large number of individual test subjects without supervision, each test subject is issued a unique identity card 38 which is encoded with sufficient information to direct the mini computer 10 to assemble the appropriate test sequence for that corresponding test subject. The encoded information may be as simple as a unique identification number for the test subject which is read by the reader 34 and compared by the mini computer 10 to an internally stored data base containing the necessary information arranged by test subject number, or, depending upon the amount of storage available on the card 38, may even include a software instruction set directing a portion of the operation of the system 8.

As will be described more particularly hereinbelow, the responses of the test subject to the queries regarding the images 12 appearing on the display 14 are recorded and evaluated by the mini computer 10 for comparison against a preselected standard of performance which is related to the level of visual skills required to be demonstrated by the test subject. Following completion of one or more visual skills screening tests, the system 8 determines if the test subject has demonstrated such required skills or not. Depending upon the environment and intended use of the screening test results, such results may be stored internally by the mini computer 10, announced to the test subject, and/or transmitted electrically to another location for evaluation by supervisory personnel.

It should also be noted that the system 8 according to the present invention, shown herein as a standalone configuration able to operate independently at a given physical location, may equivalently be configured as a series of remote monitors 16 and interfaces 20, 22, 34 controlled and directed by a central processor or mainframe computer via data transmission links, modems, or other such information transfer and control links. The system is thus embodied in the interconnection and cooperation of the individual components and not with regard to their physical location.

VISUAL ACUITY SCREENING

Figure 2:
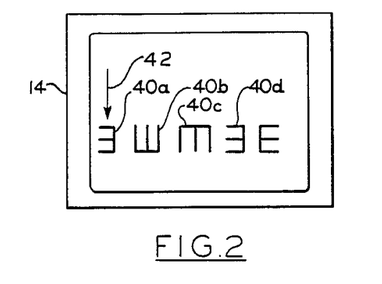
FIG. 2 illustrates the appearance of the video display of the screening system according to the present invention during a visual acuity screening test.

The system 8 according to the present invention provides a means for testing the visual acuity of an individual test subject wherein a series of video images 12 are displayed on a video display screen 14 and viewed at a fixed distance through an eye piece 26 by a test subject. A typical video display during such visual acuity testing is shown in FIG. 2 and includes a series of individual video images 40a, 40b, 40c, which are essentially similar but for a single characteristic which differs from image to image and which, for those with sufficient visual acuity, easily distinguished. In the example of FIG. 2, images 40a, 40b, 40c are the traditional E-shape, used in traditional eye test charts, oriented to point variously up, down, right, or left.

During the visual acuity test as administered by the system 8 according to the present invention, a series of such shapes 40a, 40b, 40c are displayed horizontally across the display 14 with the characteristic, for this embodiment, the direction of the pointing legs of the E-shape, being randomly distributed throughout the series in response to the direction of the controlling mini computer 10. The system 8 indicates one of the images 40a, 40b, 40c such as by generating a visual arrow 42 on the screen as shown in FIG. 2. The test subject, viewing the display 14 through the eye piece 26 is queried as to which direction the indicated shape 40a is pointing and responds via the interface 20, 22 such as by pressing an individual key corresponding to the appropriate direction, etc. It will be apparent to those familiar with visual acuity testing that, by producing a sufficiently small series of images 40a, 40b, 40c, the test designer may evaluate the test subject at nearly any level of visual skill. For this test, inability to perceive the characteristic or direction of the E-shape would indicate the limit of the test subject's visual acuity.

Based upon the particular style of video monitor 16 employed, it may be required that one of the visual filters 28 employed be a reducing lens to alter the optical characteristics of the display 14, hood 24 and eye piece 26 so as to properly test for the desired acuity. For example, a typical RGB color monitor does not produce a sufficiently distinct image to enable testing of close range visual acuity. By providing a filter, such as a reducing lens 28, between the eye piece 26 and the display 14, the system 8 according to the present invention utilizes a larger image 12 which is made to appear smaller and closer to the test subject's eyes by the optical action of the lenses 28. The particular optical characteristics of the lenses 28 is, of course, responsive to the geometry of the monitor 16 and hood 24 combination, however for one embodiment of the system 8 according to the present invention wherein the eye piece 26 is fixed at a distance of 16 inches (41 cm) from the display 14, actual images 0.152 inches (0.39 cm) in height are made to appear 14 inches (35.5 cm) from the test subject's eyes and reduced in size to screen for a visual acuity skill level of 20/25 by disposing a pair of lenses having the appropriate optical characteristics.

Figure 5:
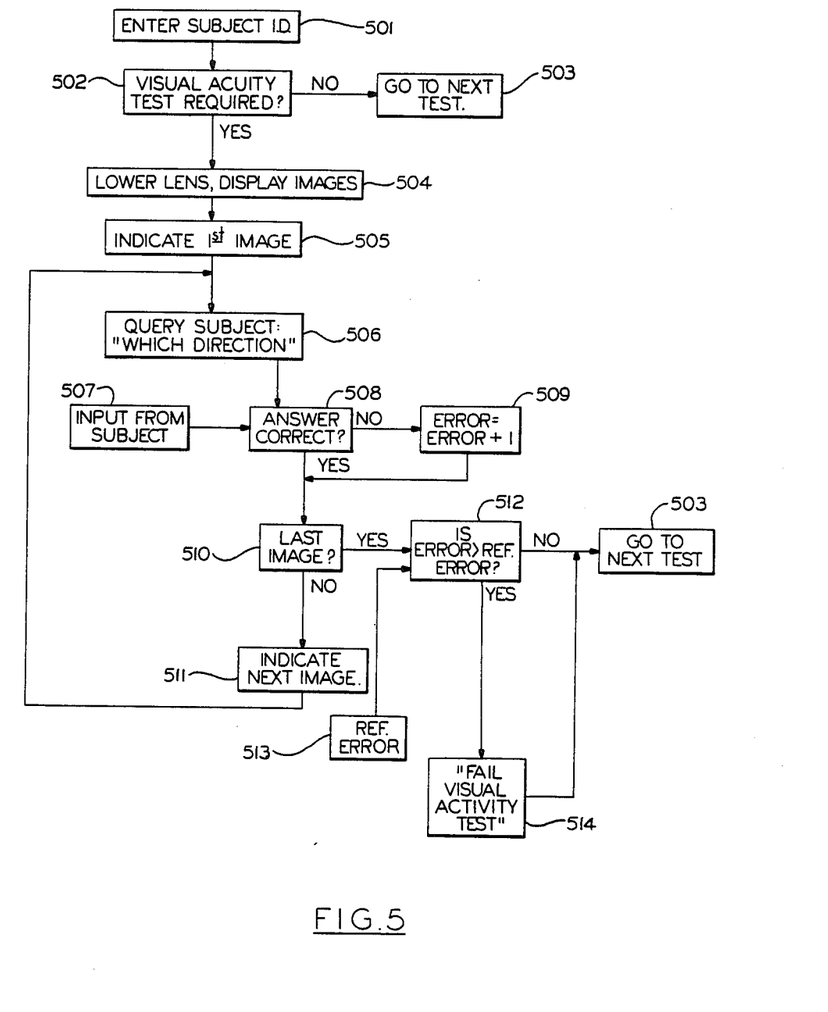
FIG. 5 is a schematic flow chart illustrating the decision logic of the visual acuity screening test.

The logic of the visual acuity testing sequence is illustrated by the flow chart shown in FIG. 5. Such flow charting is merely schematic of the logic and may be executed by any of a variety of software instruction codes or other instruction sets adapted to direct the hardware of the system 8 according to the present invention. The first step in the sequence of FIG. 5 is the entry of the test subject I.D. 501. The system determines 502 if a visual acuity test is required. If not 503, the system is directed to proceed to the next test.

If the test subject is required to demonstrate visual acuity test skills 504, the system according to the preferred embodiment lowers the reducing lenses 28 as described hereinabove and displays a series of images 40a, 40b, 40c having randomly distributed differing characteristics. The system indicates the first image 505 and queries, for the above example of the variously pointing E-shapes, the test subject as to which direction 506 each shape is indicating.

The subject provides input 507 which is compared 508 by the system with incorrect responses 509 incrementing an error flag. The system progressively displays 511 the other images, querying the test subject 506 each time until reaching the last image 510. The error flag is then compared 512 to a reference error value 513 for determining if the subject has failed 514 the visual acuity test. The determination 512 essentially signals the end of the testing and the system is referred to the next test 503 if any.

COLOR RECOGNITION SCREENING TEST

Figure 3:
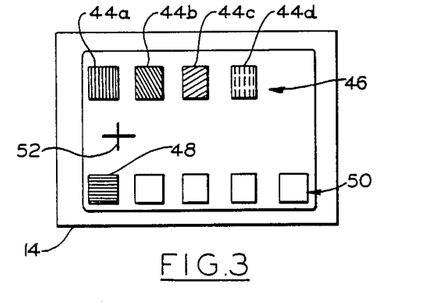
FIG. 3 shows the appearance of the video display during a color recognition screening test.

Testing for color recognition or color blindness is accomplished by displaying a series of color bars 44a, b, c, d on the video display 14. Each color bar 44a-d differs slightly in color from each other displayed color bar, with such differences being discernible by test subjects with adequate color recognition visual skills.

The test subject is requested by the system 8 to rearrange the randomly distributed color bars 44a-44d, placing the bars in order based upon perceived color. A properly skilled test subject will be able to order the random color bars with regard to the color spectrum, broadly described as red to orange to yellow to green to blue to violet to red again. In a typical arrangement the color progression is divided into four parts having fourteen equally different colors in each portion of the spectrum. Of the fourteen color bars for each portion, thirteen are presented to the test subject randomly distributed along an upper line 46 on the video display 14 as shown in FIG. 3, with one of the bars 48 representing one of the two extremities for that particular portion appearing in the lower left hand corner. The subject is instructed to move the bars 44a-d from the upper line 46 to the lower line 50 in order by color progression starting with the first block 48.

A typical human interface for accomplishing such movement is the mouse 22 which, in cooperation with mini computer 10, causes a cursor 52 to appear on the display 14 which moves in response to physical movement of the mouse 22 over a horizontal surface. The test subject moves the mouse and hence cursor 52 over a desired color bar, identifying such bar by clicking a button on the mouse 22 thereby directing the computer 10 to move the indicated color bar from the upper line 46 to the next position on the lower line 50. As will be familiar to those skilled in the art of computer-human interfacing, the software instruction set for the color recognition test according to the present invention may be easily adapted to enable the test subject to orient the individual color bars on the lower line 50 to his or her complete satisfaction. When the subject is satisfied with the arrangement appearing on the display, the computer 10 is instructed, via the interfaces 20, 22 to evaluate the final order and thereby determine of the subject has demonstrated the requisite color recognition visual skill level.

Figure 6:
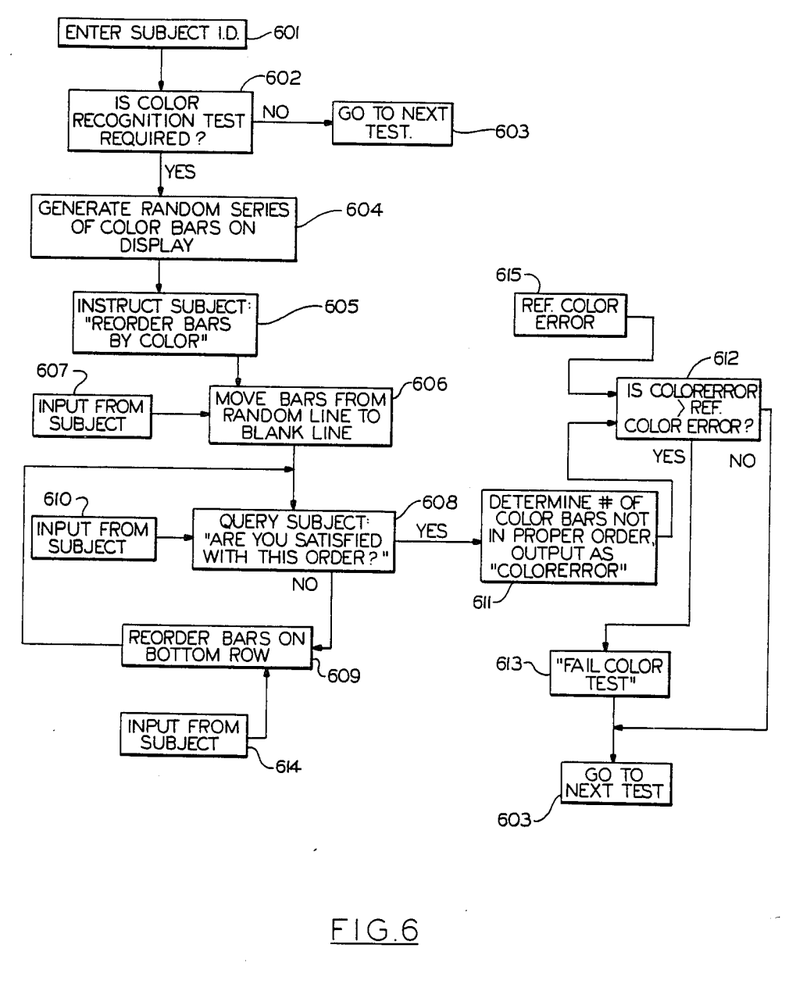
FIG. 6 is a schematic flow chart illustrating the decision logic of the color recognition screening test.

As with the visual acuity test, FIG. 6 shows the logical test sequence of the color recognition screening test starting with the entry of the test subject's identification information 601. Following a determination 602 of whether or not the color test is required, the system either goes to the next test 603 if any, or generates and displays a randomized series of color bars on the video display 604. The test subject is directed 605 to rearrange the bar's color which is accomplished by moving the bars from the upper, random line to the lower, initially blank line 606 in response to input from the test subject 607.

In the system 8 according to the present invention, the subject is then queried 608 as to whether or not he or she is satisfied with the arrangement appearing on the display. If not, the subject is allowed 609, 614 to rearrange the color bars appearing on the bottom line being repeatedly queried 608 until such time as the response 610 indicates satisfaction. Upon receiving such indication 610 that the arrangement is satisfactory to the test subject, the system determines 611 the number of color bars in the final, satisfactory arrangement which are not properly arranged in sequential order. The result, termed "color error" is compared 612 to a reference level 615 of permissible color error for determining if the test subject failed 613 the color test. Following such determination the system is directed 603 to pass onto the next visual skills test sequence, if any.

DEPTH PERCEPTION SCREENING TEST

Figure 4A:
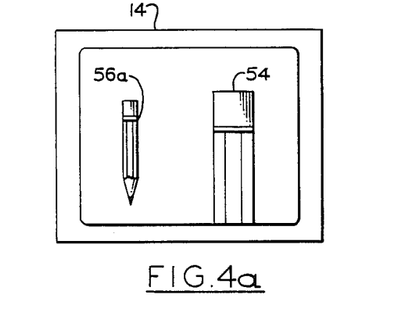
FIGS. 4a, 4b, and 4c show selected video frames during a depth perception screening test.
Figure 4B:
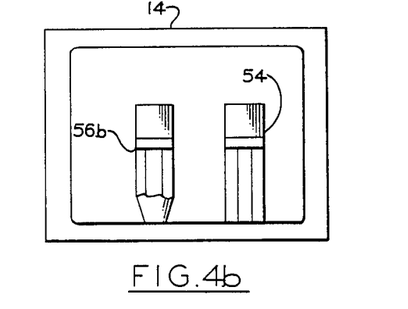
Figure 4C:
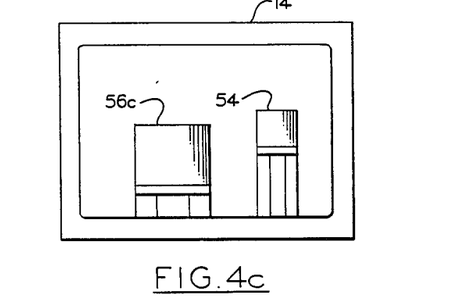

FIGS. 4a, 4b, and 4c represent three of a series of visual images generated by the system 8 on the video display 14 for testing the ability of the test subject to judge the relative depths or distances of two objects. The display 14 shows two images, the right image 54 being apparently immobile and fixed in space, and the left image 56a moving as the series of individual frames is displayed. The images 54, 56a represent common objects known to the test subject such as a lead pencil as illustrated in FIG. 4a. The movable, or left image 56a differs from the right image 54 by being an image of a used pencil having a shortened longitudinal dimension resulting from repeated sharpenings.

During the test procedure, the right hand image 54 is held immobile while the left hand image 56a, b, c appears to approach from the background 56a to being equidistant 56b with the immobile object 54, to being in the foreground 56c. During the progression 56a, b, c the subject is asked to indicate, via the human interface, when the test subject believes the movable image 56b to appear to be equidistant from the eye piece 28 with the immobile object 54. At such indication, the progression of frames is ceased and the subject is queried as to whether or not he or she is satisfied with the appearance of the display 14 as showing equidistant right and left hand objects.

If the subject is not satisfied, the test sequence is restarted from FIG. 4a and the progression ceasing and querying steps repeated until such time as the subject expresses satisfaction with the display. Evaluation of the depth perception test is relatively straightforward, with the test system 8 merely determining the number of frames between the actual reference frame in which the objects are in fact illustrated as being equidistant and the frame appearing on the display 14 at the time the subject stopped the progression.

Before discussing the logic of the test procedure, it is necessary to note that the depth perception test discussed hereinabove is in fact presenting the test subject with only an illusion of differing distance images on the display 14 and does not present a true stereoscopic image of the images to the test subject. Thus, the test sequence shown in FIGS. 4a-4b tests the three dimensional perception of the test subject by means of a two dimensional image. Despite this apparent shortcoming, comparison of the results of the depth perception test according to the present invention and a standard manual depth perception test wherein the subject is asked to judge the relative distance of two physical objects moved manually by a test coordinator, the two dimensional image test according to the present invention has proved to accurately screen out those individuals who are unable to judge relative distances of actual objects.

Figure 7:
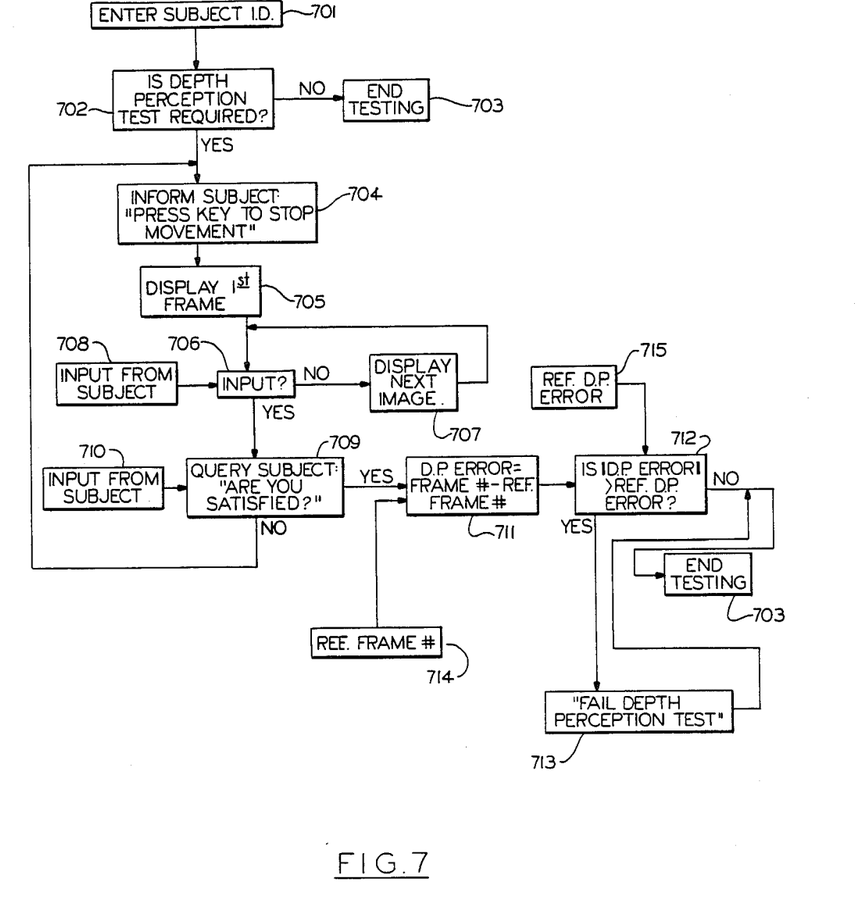
FIG. 7 is a schematic flow chart illustrating the decision logic of the depth perception screening test.

FIG. 7 shows a schematic of the logic flow diagram of the depth perception screening test as administered by the system 8 according to the present invention. As with the preceding tests, the test subject I.D. 701 is entered and a determination 702 is made by the system as to whether or not a depth perception test is required of the individual. If not, the test sequence is ended 703. If required, the subject is directed 704 to press any key on the keyboard interface 20 to stop the movement of the images on the display 14. The system displays 705 a first frame of a sequence of frames depicting the movement illustrated in FIGS. 4a-4c, and monitors the keyboard 706 to determine if any input has been initiated by the test subject. If not, the system displays 707 subsequent images continually monitoring 706 for input 708 from the test subject. Upon receiving such input 708, the subject is queried 709 as to whether or not he or she is satisfied with the image displayed on the screen. In response to such query 709 the subject indicates yes or no 710. If not, the system resets to the first frame 705 and repeats the test sequence 706, 707. If the subject is satisfied, a depth perception error value is determined 711 by calculating the difference between the frame number displayed and indicated as being satisfactory to the test subject and a reference frame number 714 in which both the left and right images are depicted as being equidistant. If the absolute value of such depth perception error as calculated 711 is greater than 712 a reference level depth perception error 715, the subject is determined to have failed 713 the depth perception test. The test sequence is then ended 703 and the subject may be informed of the test results if desired.

CONCLUSION

As will be appreciated by reviewing the above test logic and descriptions, the system 8 according to the present invention is designed to quickly and economically screen individuals to identify those individuals and the corresponding potential deficiencies which must be further evaluated by trained personnel. The various error levels and passing reference test scores should thus be established by the overall test supervisor as being sufficiently high so as to insure that any individual test subject passing the appropriate visual skills screening test as administered by the system 8 according to the present invention is thus certain to possess the required visual skills desired. A failure of any one of such visual skills screening tests merely indicates that the subject should be evaluated by a skilled professional who may judge the subject as being adequately skilled and/or prescribe corrective lenses or treatment for raising the quality of the subject's visual skills to the required level.

The present invention is thus well adapted to achieve the objects and advantages as set forth hereinabove, and, although disclosed in a single embodiment particularly suited for large scale, distributed testing in an industrial environment, may be equally well adapted by various equivalent modifications and embodiments to provide small scale, portable, field, or similar testing in a variety of private or public settings depending upon the individual needs and requirements of the testing organization.

Other visual skills beyond the three described above may be measured by the system which may, depending upon the computer instruction set and degree of sophistication of the testing organization, be configured to provide additional or in depth testing in response to a detected potential visual skill deficiency of a particular test subject. As noted above and restated here, the preferred embodiment of the system 8 according to the present invention shown and described hereinabove is thus only intended to be an illustration of a particular embodiment of the inventive concept and is not to be construed in any sense as limiting the scope of the invention except as recited in the following claims.

We claim:

1. An automatic optical testing system for screening individual test subjects for visual deficiencies, including
   a color video monitor,
   a human interface,
   means for identifying and determining test requirements for each individual test subject,
   a mini computer linked to the human interface, video monitor and the identifying means, including one or more instruction sets, each instruction set particularly adapted for generating a series of video images to measure the test subject for a corresponding visual defect, said one or more instruction sets being selected, responsive to the individual test subject's determined test requirements, from a group of instruction sets consisting of:
   (a) a visual acuity testing instruction set including
      (1) steps for generating a plurality of images on the video monitor, each image having a randomly differing characteristic,
      (2) steps, responsive to manipulation of the human interface by the test subject, for querying the test subject regarding the characteristic of each image,
      (3) steps for generating a visual acuity score responsive to the actual characteristic of each image and the corresponding test subject response;
   (b) a color recognition testing instruction set including
      (1) steps for generating a randomly arranged plurality of progressively incremental color bars on the video monitor,
      (2) steps, responsive to manipulation of the human interface, for rearranging the plurality of color bars on the video monitor, wherein the test subject is directed to arrange the color bars in sequential order of color increment,
      (3) steps, responsive to a final arrangement of the color bars as approved by the test subject, for generating a color recognition score; and
   (c) a depth perception testing instruction set, including
      (1) steps for generating a series of frames on the video monitor, the series of frames including two visual images, each image appearing at an apparent distance from the test subject, wherein the series of frames progressively shows the visual images at relative apparent distances ranging from one image more distant than the other image to the one image being nearer than the other image,
      (2) steps for displaying the series of frames on the video monitor and for directing the test subject to respond via the human interface when the one image and the other image appear to be equidistant, and
      (3) steps, responsive to the accuracy of the response of steps(c) (2) for generating a depth perception score; and
      (4) means, responsive to the test scores determined by each selected instruction set and an established, corresponding passing score value, for determining if the test subject being screened meets or falls below the corresponding passing score.

2. An automated optical testing system for screening individual test subjects for visual deficiencies, comprising:
   a color video display,
   a hood, secured to the video display and including an eye piece for receiving and positioning the face of a person to be tested,
   visual acuity testing means, interactive with the test subject and the video display, for generating a plurality of differing optical images to be displayed on the video display, said generating means further including means for recording a corresponding plurality of responses from the test subject,
   color recognition testing means, interactive with the test subject and the video display, for generating a randomly arranged series of color bars on the video display, said color recognition means, in response to interaction with the test subject, adapted to rearrange said series of color bars, and wherein said color recognition means further comprises means, responsive to the arrangement established from the test subject's interaction for determining the number of color bars not arranged progressively in series by color, and depth perception testing means, interactive with the video display and the test subject, for generating a pair of images on the video display, one of the images being apparently stationary, the other image apparently moving depthwise in space with said apparent movement controlled, at least in part, by interaction of the test subject with the depth perception testing means, the depth perception testing means further comprising:

means for determining the difference between the apparent depth of the one image and the other image as a result of the test subject's interaction, and means responsive to the visual acuity testing means, color recognition testing means, and depth perception testing means, for determining the existence of a visual deficiency in the test subject.

3. The system as recited in claim 2, further including means, disposed within the hood adjacent the eye piece, for selectively positioning at least one optical filter between the test subject's eyes and the video display in response to the visual acuity testing means.

4. The system as recited in claim 2, wherein the visual acuity testing means, the color discrimination testing means, and the depth perception testing means are integrated into a single computer means including a software instruction set, human interface means for receiving information from the test subject, and means for generating a video signal input to the video display means.

5. The system as recited in claim 4, wherein the video signal generating means includes a video laser disk player.

6. The system as recited in claim 2, further comprising:

means for determining the identity and test requirements for each individual test subject.

7. The system as recited in claim 6 wherein the test subject identification means includes a plurality of identity cards uniquely assigned to each individual test subject and means for reading each unique identity card to determine the corresponding test sequence for the corresponding test subject.

8. An automated optical testing system for screening individual test subjects for visual deficiencies, comprising:

a color video display, a hood, secured to the video display and including an eye piece for receiving and positioning the face of a person to be tested, color recognition testing means, interactive with the test subject and the video display, for generating a randomly arranged series of color bars on the video display, said color recognition means, in response to interaction with the test subject, adapted to rearrange said series of color patches, and wherein said color recognition means further comprises means, responsive to the arrangement established from the test subject's interaction for determining the number of color bars not arranged progressively in series by color, and means, responsive to the color recognition testing means, for determining the existence of a visual deficiency in the test subject.

9. An automated optical testing system for screening individual test subjects for visual deficiencies, comprising:

a video display, a hood, secured to the video display and including an eye piece for receiving and positioning the face of a person to be tested, depth perception testing means, interactive with the video display and the test subject, for generating a pair of images on the video display, one of the images being apparently stationary, the other image apparently moving depthwise in space with said apparent movement controlled, at least in part, by interaction of the test subject with the depth perception testing means, the depth perception testing means further comprising:

means for determining the difference between the apparent depth of the one image and the other image as a result of the test subject's interaction, and means responsive to the depth perception testing means, for determining the existence of a visual deficiency in the test subject.

* * * * *